(12) United States Patent
Morita et al.

(10) Patent No.: US 9,480,668 B2
(45) Date of Patent: Nov. 1, 2016

(54) BLOOD FLOW PROMOTING AGENT

(71) Applicant: KYOWA HAKKO BIO CO., LTD., Tokyo (JP)

(72) Inventors: Masahiko Morita, Tokyo (JP); Ayako Kamimura, Tokyo (JP); Yoshinori Kobayashi, Sagamihara (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 0 days.

(21) Appl. No.: 14/440,260

(22) PCT Filed: Nov. 5, 2013

(86) PCT No.: PCT/JP2013/079904
§ 371 (c)(1),
(2) Date: May 1, 2015

(87) PCT Pub. No.: WO2014/069660
PCT Pub. Date: May 8, 2014

(65) Prior Publication Data
US 2015/0297546 A1    Oct. 22, 2015

(30) Foreign Application Priority Data

Nov. 5, 2012 (JP) .................................. 2012-243913

(51) Int. Cl.
| | |
|---|---|
| A61K 31/198 | (2006.01) |
| A61K 8/44 | (2006.01) |
| A61Q 19/00 | (2006.01) |
| A61K 31/17 | (2006.01) |
| A61K 8/42 | (2006.01) |

(52) U.S. Cl.
CPC ............... A61K 31/198 (2013.01); A61K 8/42 (2013.01); A61K 8/44 (2013.01); A61K 31/17 (2013.01); A61Q 19/00 (2013.01)

(58) Field of Classification Search
None
See application file for complete search history.

(56) References Cited

PUBLICATIONS

Ruiz et al., British Journal of Pharmacology, 125: 186-192 (1998).
Yamaguchi et al., Hokkaido Journal of Dental Science, 32(1): 2-11 (2011).
Yang et al., Cell Metabolism, 12: 130-141 (2010).
Japanese Patent Office, International Search Report in International Patent Application No. PCT/JP2013/079904 (Feb. 10, 2014).

Primary Examiner — Brian J Davis
(74) Attorney, Agent, or Firm — Leydig, Voit & Mayer, Ltd.

(57) ABSTRACT

The present invention provides a blood flow promoting agent containing citrulline or a salt thereof and capsaicin or capsaicinoids as active ingredients, which is safe even by long-term administration, a food with health claims and a functional food affording such action, particularly, a blood flow promoting agent exhibiting an effective vasodilatory action of capsaicin at a low dose free of irritant property, which can be applied to improvement of athletic performance exhibited in relation to peripheral vasodilatation, suppression of fat accumulation, improvement of skin quality, as well as securing blood circulation in ischemic disease and the like, relaxation of blood vessel biased to coarctation due to advancing age, lifestyle-related diseases and the like, prophylaxis of arteriosclerosis, and prophylaxis of stiff neck, feeling of cold, erectile dysfunction, thrombosis and the like due to blood flow disorder.

11 Claims, 1 Drawing Sheet

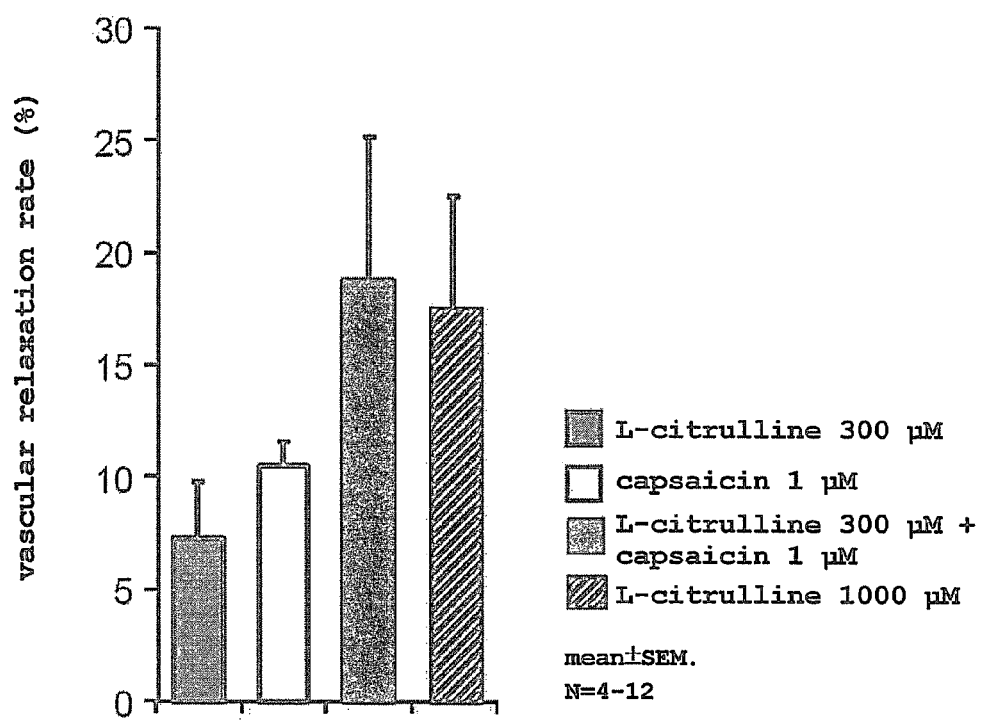

US 9,480,668 B2

BLOOD FLOW PROMOTING AGENT

CROSS-REFERENCE TO RELATED APPLICATIONS

This patent application is the U.S. national phase of International Patent Application No. PCT/JP2013/079904, filed Nov. 5, 2013, which claims the benefit of Japanese Patent Application No. 2012-243913, filed on Nov. 5, 2012, which are incorporated by reference in their entireties herein.

TECHNICAL FIELD

The present invention relates to a more effective blood flow promoting agent having a vasorelaxing action and a functional food having such action.

BACKGROUND ART

Citrulline is one kind of amino acid which is not used as a synthetic starting material of protein and present as a free form in the body. In the body, it plays an important role as an arginine precursor for biosynthesis of arginine or as a constituent factor of NO cycle involved in the supply of nitric oxide (NO).

Citrulline has been reported to have a vasodilating action since it shows a relaxation action on the vascular smooth muscle of rabbit (non-patent document 1). It is said to have various other effects such as suppression of arteriosclerosis, improvement of cold feeling, energy enhancement, ammonia detoxification and the like.

Capsaicin (8-methyl-N-vanillyl-6-nonenamide) and dihydrocapsaicin (8-methyl-N-vanillyl-nonanamide) are pungent taste components contained in chili pepper. They have long been used as a spice for foods, and a counterirritant for medical treatments. In addition, they have physiological activities such as promotion of appetite, analgesic action and the like. In recent years, it has been reported that administration of capsaicin activates TRPV1 (Transient Receptor Potential Vanilloid 1), enhances endothelial-dependent vascular relaxation and prevents hypertension (non-patent document 2).

Capsaicin is known to have a strong pungent taste and irritant property. According to a study relating to a sublingual treatment with a capsaicin solution, irritant saliva secretion due to capsaicin is promoted in a concentration-dependent manner, and when the concentration of capsaicin solution is not less than 75 µM, a feeling of strong pain was produced in a concentration-dependent manner (non-patent document 3). Thus, use of capsaicin for foods and pharmaceutical products is limited due to its strong pungent taste, irritant property and poor solubility.

The concentration range of capsaicin that does not stimulate animal tissues is not more than several dozen µM and, as mentioned above, while the development of a method of effectively potentiating action by a combination of capsaicin in a low concentration range free of irritant property and known material is useful but has not been known heretofore.

DOCUMENT LIST

Non-Patent Document non-patent document 1:"British Journal of Pharmacology", 1998, vol. 125, p. 186-192 non-patent document 2:"Cell Metabolism", 2010, vol. 12, p. 130-141 non-patent document 3:"Hokkaido journal of dental science", 2011, vol. 32, p. 2-11

SUMMARY OF THE INVENTION

Problems to be Solved by the Invention

The present invention aims to provide a blood flow promoting agent comprising citrulline or a salt thereof and capsaicin or capsaicinoids as active ingredients, which enhances the effect of citrullin, and is more effective in a concentration range where capsaicin or capsaicinoids are free of irritant property.

Means of Solving the Problems

The present inventors have conducted intensive studies in an attempt to solve the aforementioned problems and found that the use of a small amount of a combination of citrulline or a salt thereof and capsaicin or capsaicinoids relaxes vascular smooth muscle and thus expands blood vessels, and a blood flow promoting agent containing them is useful. They have conducted further studies and completed the present invention.

Accordingly, the present invention relates to the following [1]-[28].

[1] A blood flow promoting agent comprising citrulline or a salt thereof and capsaicin or capsaicinoids as active ingredients.

[2] The blood flow promoting agent of [1], wherein the dose of capsaicin or capsaicinoids is an amount free of irritant property.

[3] The blood flow promoting agent of [1], wherein the amount free of irritant property is 0.1 mg-20 mg per dose for an adult.

[4] The blood flow promoting agent of any one of [1]-[3], wherein the dose of citrulline or a salt thereof is 20 mg-2000 mg per dose for an adult.

[5] The blood flow promoting agent of any one of [1]-[4], wherein citrulline or a salt, thereof is contained in a proportion of 10-200 parts by weight per 1 part by weight of capsaicin or capsaicinoids.

[6] The blood flow promoting agent of [5], which is in a unit package form for one meal, wherein the unit contains, an ingestion amount for one time, 20 mg-2000 mg of citrulline or a salt thereof, and 0.1 mg-20 mg of capsaicin or capsaicinoids.

[7] The blood flow promoting agent of any one of [1]-[6], which is used for improvement of athletic performance exhibited in relation to peripheral vasodilatation, suppression of fat accumulation, improvement of skin quality, or prophylaxis of ischemic disease.

[8] A method of promoting blood flow, comprising a step of administering citrulline or a salt thereof and capsaicin or capsaicinoids to a subject in need thereof.

[9] The method of [8], wherein the dose of capsaicin or capsaicinoids is an amount free of irritant property.

[10] The method of [9], wherein the amount free of irritant property is 0.1 mg-20 mg per dose for an adult.

[11] The method of any one of [8]-[10], wherein the dose of citrulline or a salt thereof is 20 mg-2000 mg per dose for an adult.

[12] The method of any one of [8]-[11], wherein citrulline or a salt thereof is contained in a proportion of 10-200 parts by weight per 1 part by weight of capsaicin or capsaicinoids.

[13] The method of [12], wherein administration of capsaicin or capsaicinoids is in a unit package form for one meal, wherein the unit contains, an ingestion amount for one time, 20 mg-2000 mg of citrulline or a salt thereof, and 0.1 mg-20 mg of capsaicin or capsaicinoids.

[14] The method of any one of [8]-[13], which is used for improvement of athletic performance exhibited in relation to peripheral vasodilatation, suppression of fat accumulation, improvement of skin quality, or prophylaxis of ischemic disease.

[15] Citrulline or a salt thereof and capsaicin or capsaicinoids for use for promoting blood flow.

[16] The citrulline or a salt thereof and capsaicin or capsaicinoids of [15], wherein the dose of capsaicin or capsaicinoids is an amount free of irritant property.

[17] The citrulline or a salt thereof and capsaicin or capsaicinoids of [16], wherein the amount free of irritant property is 0.1 mg-20 mg per dose for an adult.

[18] The citrulline or a salt thereof and capsaicin or capsaicinoids of any one of [15]-[17], wherein the dose of citrulline or a salt thereof is 20 mg-2000 mg per dose for an adult.

[19] The citrulline or a salt thereof and capsaicin or capsaicinoids of any one of [15]-[18], wherein citrulline or a salt thereof is contained in a proportion of 10-200 parts by weight per 1 part by weight of capsaicin or capsaicinoids.

[20] The citrulline or a salt thereof and capsaicin or capsaicinoids of [19], which is in a unit package form for one meal, wherein the unit contains, an ingestion amount for one time, 20 mg-2000 mg of citrulline or a salt thereof, and 0.1 mg-20 mg of capsaicin or capsaicinoids.

[21] The citrulline or a salt thereof and capsaicin or capsaicinoids of any one of [15]-[20], which is used for improvement of athletic performance exhibited in relation to peripheral vasodilatation, suppression of fat accumulation, improvement of skin quality, or prophylaxis of ischemic disease.

[22] Use of citrulline or a salt thereof and capsaicin or capsaicinoids for the production of a blood flow promoting agent.

[23] The use of [22], wherein the dose of capsaicin or capsaicinoids is an amount free of irritant property.

[24] The use of [23], wherein the amount free of irritant property is 0.1 mg-20 mg per dose for an adult.

[25] The use of any one of [22]-[24], wherein the dose of citrulline or a salt thereof is 20 mg-2000 mg per dose for an adult.

[26] The use of any one of [22]-[25], wherein the blood flow promoting agent comprises citrulline or a salt thereof in a proportion of 10-200 parts by weight per 1 part by weight of capsaicin or capsaicinoids.

[27] The use of [26], wherein the blood flow promoting agent is in a unit package form for one meal, wherein the unit contains, an ingestion amount for one time, 20 mg-2000 mg of citrulline or a salt thereof, and 0.1 mg-20 mg of capsaicin or capsaicinoids.

[28] The use of any one of [22]-[27], wherein the blood flow promoting agent is for the improvement of athletic performance exhibited in relation to peripheral vasodilatation, suppression of fat accumulation, improvement of skin quality, or prophylaxis of ischemic disease.

EFFECT OF THE INVENTION

Since the blood flow promoting agent of the present invention shows an effective vasodilating action at a low dose and does not show the irritant property of capsaicin since citrulline is used in combination, and contains amino acid and a component derived from food as active ingredients, the agent is superior in safety, permits long-term administration, and can be regularly ingested, particularly when it is a food with health claims.

In addition, since the blood flow promoting agent of the present invention has a superior vasorelaxing action, it can be applied to improvement of athletic performance exhibited in relation to peripheral vasodilatation, suppression of fat accumulation, improvement of skin quality, as well as securing blood circulation in ischemic disease and the like, relaxation of blood vessel biased to coarctation due to advancing age, lifestyle-related diseases and the like, prophylaxis of arteriosclerosis, and prophylaxis of stiff neck, feeling of cold, erectile dysfunction, thrombosis and the like due to blood flow disorder.

BRIEF DESCRIPTION OF THE DRAWINGS

FIG. 1 shows vascular relaxation rate (%) of artery isolated from rat, when each sample is added to vasoconstriction induced by 0.3 μM Norepinephrine.

DESCRIPTION OF EMBODIMENTS

The present invention relates to a blood flow promoting agent containing citrulline or a salt thereof and capsaicin or capsaicinoids as active ingredients (hereinafter sometimes to be abbreviated as the blood flow promoting agent of the present invention).

In the present invention, "promotion of blood flow" means increasing the blood amount of any tissue or increasing the blood circulation amount per unit time when an increase in the blood flow from a normal state can be medically and physiologically beneficial, and recovering the blood amount of any tissue to normal or recovering the blood circulation amount per unit time of any tissue to normal when recovery from the state of low blood flow can be medically and physiologically beneficial.

The blood flow promoting agent of the present invention has a particular function of pharmaceutical products, health aid foods, foods with health claims, supplements and the like, which are used for "promoting blood flow", and means a composition similar to a pharmaceutical product and functional food, which are ingested for the purpose of maintaining health and the like.

Citrulline or a salt thereof to be used in the present invention may be any of L-form, D-form and DL-form, with preference given to L-form.

Citrulline can also be obtained by purchasing a commercially available product. Examples of a method of chemically synthesizing citrulline include the methods described in J. Biol. Chem., 122, 477(1938), J. Org. Chem., 6, 410 (1941) and the like. Examples of the method of producing L-citrulline by fermentation include the methods described in JP-A-53-075387, JP-A-63-068091 and the like. L-citrulline and D-citrulline can also be purchased from Sigma-Aldrich Co. LCC. and the like.

Examples of the salt of citrulline include acid addition salt, metal salt, ammonium salt, organic amine addition salt, amino acid addition salt and the like.

Examples of the acid addition salt include inorganic acid salts such as hydrochloride, sulfate, nitrate salt, phosphate and the like, and organic acid salts such as acetate, maleate, fumarate, citrate, malate, lactate, α-ketoglutarate, gluconate, caprylate and the like.

Examples of the metal salt include alkali metal salts such as sodium salt, potassium salt and the like, alkaline earth metal salts such as magnesium salt, calcium salt and the like, aluminum salt, zinc salt and the like.

Examples of the ammonium salt include salts such as ammonium, tetramethylammonium and the like.

Examples of the organic amine addition salt include salts with morpholine, piperidine and the like.

Examples of the amino acid addition salt include salts with glycine, phenylalanine, lysine, aspartic acid, glutamic acid and the like.

In the present invention, malate is preferably used as a salt of citrulline, but other salt, or two or more salts may be used in an appropriate combination.

Citrulline or a salt thereof in the present invention may be produced by any production methods such as protein hydrolysis method, chemical synthesis method, enzyme method, fermentation method and the like, or a commercially available product can also be used.

Citrulline or a salt thereof in the present invention can also be obtained by enzymatically hydrolyzing natural protein having the amino acid sequence.

As capsaicinoids in the present invention, any of capsaicin or capsaicinoids produced by a production method such as chemical synthesis method, enzymatical synthesis method and the like, commercially available products, and those extracted and purified from naturally occurring substances can be used. Examples of the naturally occurring substance include fruits of plants belonging to the genus Capsicum such as chili pepper and the like.

Capsaicinoids in the present invention include nordihydrocapsaicin, dihydrocapsaicin, and compound derived from capsinoid (capsiate), and preferred are dihydrocapsaicin and capsiate.

The blood flow promoting agent of the present invention can be applied to human, animals other than human [for example, mammals other than human (domestic animals and pet animals such as swine, bovine, horse, dog and the like), birds (poultry and pet animals such as turkey, chicken and the like) and the like] and the like.

The blood flow promoting agent of the present invention contains citrulline or a salt thereof and capsaicin or capsaicinoids in combination (i.e., concomitant drug), and may be any as long as citrulline and the like and capsaicin and the like can be combined at the time of administration. Therefore, as long as the blood flow promoting agent of the present invention permits combination of citrulline or a salt thereof and capsaicin or capsaicinoids at the time of administration, it may be a single preparation obtained by simultaneously formulating citrulline and the like and capsaicin and the like, or a combination of two kinds of preparations obtained by separately formulating citrulline and the like and capsaicin and the like. The administration form is not particularly limited and examples thereof include (1) administration of a composition containing citrulline and capsaicin, i.e., administration of a single preparation, (2) simultaneous administration of two kinds of preparations of citrulline and capsaicin, which have been separately formulated, by the same administration route, (3) administration of two kinds of preparations of citrulline and capsaicin, which have been separately formulated, by the same administration route in a staggered manner (e.g., administration in the order of citrulline and capsaicin, or administration in a reverse order), (4) simultaneous administration of two kinds of preparations of citrulline and capsaicin, which have been separately formulated, by different administration routes, (5) administration of two kinds of preparations of citrulline and capsaicin, which have been separately formulated, by different administration routes in a staggered manner (for example, administration in the order of citrulline and capsaicin or in the reverse order) and the like.

In the case of administration in a staggered manner, it is necessary that the both are co-present in the body.

In the blood flow promoting agent of the present invention, the ratio of combination of citrulline or a salt thereof and capsaicin or capsaicinoids is generally 10-200 parts by weight, preferably 50-200 parts by weight, more preferably 100-200 parts by weight, of the content of citrulline or a salt thereof relative to 1 part by weight of capsaicin or capsaicinoids, whether the two form a single preparation or separate preparations.

In the blood flow promoting agent of the present invention, the dose (effective amount) of total of citrulline or a salt thereof and capsaicin or capsaicinoids is generally 30 mg-30 g, preferably 100 mg-10 g, particularly preferably 200 mg-3 g, per day for an adult, which is administered in one to several portions.

The dose (effective amount) of citrulline or a salt thereof is generally 20 mg-20 g, preferably 100 mg-5 g, more preferably 200 mg-2 g, per day for an adult. For administration once to several times per day, the dose (effective amount) of citrulline as a single dose (effective amount) for an adult is, for example, generally 20 mg-2000 mg, preferably 40 mg-1000 mg, more preferably 80 mg-500 mg, particularly preferably 100 mg-400 mg, for administration once per day. For example, for administration twice per day, it is generally 10 mg-1000 mg, preferably 20 mg-500 mg, more preferably 40 mg-250 mg, particularly preferably 50 mg-200 mg.

As the dose (effective amount) of capsaicin or capsaicinoids, an amount free of irritant property is used. In the present invention, "free of irritant property" means that the administered test subject does not gain a feeling of invaded stimulation such as pungent, pain and the like of the level causing pain in the test subject in any tissue involved in the process from the ingestion to metabolism.

The dose (effective amount) of capsaicin or capsaicinoids free of irritant property is generally 0.1 mg-200 mg, preferably 0.3 mg-150 mg, more preferably 0.5 mg-100 mg, per day for an adult. For administration once to several times per day, the dose (effective amount) of capsaicin or capsaicinoids as a single dose (effective amount) for an adult is generally 0.1 mg-20 mg, preferably 0.2 mg-10 mg, more preferably 0.5 mg-4 mg, for administration once per day. For example, for administration twice per day, it is generally 0.05 mg-10 mg, preferably 0.1 mg-5 mg, more preferably 0.25mg-2 mg.

The above-mentioned single dose for an adult can be appropriately changed in consideration of the condition of the body such as sex, age, disease and the like.

In the blood flow promoting agent of the present invention, the above-mentioned daily dose can be administered at once or in several portions. While the dosing period is not particularly limited, long-term administration is possible since the components are amino acid and components derived from food. It is generally 1 day-1 year, preferably 1 week-3 months.

The dosage form of the blood flow promoting agent of the present invention is not particularly limited, and may be any of oral preparation and parenteral preparation. Examples of the dosage form thereof include agents for oral administration such as tablet, granule, powder, capsule, elixir, syrup, microcapsule, drinkable preparation, emulsion, or suspension and the like, skin external preparations such as ointment, cream, gel, liquid, lotion, facial mask, bath additive and the like, injection and the like.

When orally administered, the blood flow promoting agent of the present invention can contain, where necessary, carrier, excipient, binder, swelling agent, lubricant, sweetening agent, flavor, preservative, emulsifier, coating agent and the like, and can be used together with these in a unit dosage form required to practice generally-acknowledged preparations. The amount of citrulline or a salt thereof and capsaicin or capsaicinoids in these compositions or preparations may be such an amount that affords a suitable dose within the specified range. When the agent is administered orally, it may be administered before meal, after meal or between meals.

Examples of the specific component that can be contained in the blood flow promoting agent of the present invention include binders such as tragacanth, gum arabic, cornstarch, pullulan and gelatin; excipients such as microcrystalline cellulose, crystalline cellulose and cyclic oligosaccharide; swelling agents such as cornstarch, pregelatinized starch, alginic acid and dextrin; lubricants such as magnesium stearate and calcium stearate; flowability improving agents such as fine silicon dioxide and methylcellulose; lubricants such as glycerol fatty acid ester; sweetening agents such as sucrose, lactose, aspartame and erythritol; flavors such as peppermint, vanilla flavor, cherry and orange; pH adjusters such as citric acid; emulsifiers such as monoglyceride, polyglycerol fatty acid ester, sucrose fatty acid ester, lecithin and the like; and the like.

When the dosage unit form is a capsule, the materials of the above-mentioned types can further contain liquid carriers such as fats and oils.

Moreover, various other materials can be contained to change physical form of the dosage unit. Examples of the coating agent for tablet include shellac, sugar or both and the like. As syrup or elixir, for example, sucrose as a sweetening agent, methylparaben and propylparaben as a preservative, dye and cherry or orange flavor and the like, and the like can be contained. Besides these, various vitamins, various amino acids such as arginine, alanine, glycine, leucine, isoleucine, valine and the like may also be contained.

When an enteric preparation is produced, for example, it can be produced by a conventional method and using an aqueous solution of hydroxyphenylmethylcellulose as a pre-coating treatment agent, and an aqueous solution of hydroxypropylmethylcellulose phthalate and an aqueous solution of polyacetin as coating agents.

The blood flow promoting agent of the present invention contains citrulline or a salt thereof and capsaicin or capsaicinoids as active ingredients and may further contain any other active ingredients.

For parenteral administration, for example, a solution containing citrulline and capsaicin can be nasally sprayed, administered as an injection and the like. Alternatively, when the blood flow promoting agent of the present invention is processed into a skin external preparation, citrulline and capsaicin may be dispersed in various bases and formulated by a conventional method. Examples of the base include higher fatty acid esters such as petrolatum, liquid paraffin, isopropyl myristate, octyldodecyl myristate and the like, higher alcohols such as squalane, lanolin, cetanol and the like, oleaginous bases such as silicone oil, oil from plant or animal and the like, lower alcohols such as ethanol and the like, polyvalent alcohols such as polyethylene glycol, propylene glycol and the like, emulsifiers or emulsion stabilizers such as α-monoglycerylether, lecithin, sorbitan ester of fatty acid, dextrin fatty acid ester, fatty acid monoglyceride, fatty acid metal salt, magnesium sulfate and the like, various efficacious agents such as aromatic, preservative, dye, thickener, antioxidant, UV protective agent, wound healing agent, anti-inflammatory agent, moisturizer and the like, water and the like.

In the present invention, a pharmaceutical product may be the blood flow promoting agent of the present invention per se, or may contain other additives and the like.

When the blood flow promoting agent of the present invention is used as a food, it means a health food to be ingested taking note of the particular function of the present invention, or a food for specified health uses or food with nutrient function claims defined in the food with health claims system, and further includes dietry supplements. While the amount bf citrulline and capsaicin contained in a food is not particularly limited, the amount of food and drink taken per day is preferably such amount that sets their amounts to fall within the range of the above-mentioned dose (effective amount) in the blood flow promoting agent of the present invention. The form of the blood flow promoting agent of the present invention as a food with health claims is not particularly limited.

Examples of the food in the present invention include a form wherein citrulline and capsaicin are packed in the form of an ingestion unit for one meal, a form wherein citrulline and capsaicin are suspended or dissolved to give a drink, which is packed in a bottle etc. for a single consumption and the like. The dose for one meal may be the daily dose (effective amount) shown above.

Specifically, in a unit package form for one meal, a single ingestion amount (effective amount) of the unit citrulline or a salt thereof is generally 20 mg-2000 mg, preferably 40 mg-1000 mg, more preferably 80 mg-500 mg, particularly preferably 100 mg-400 mg. For example, for ingestion twice per day, a single ingestion amount (effective amount) of the unit citrulline or a salt thereof is generally 10 mg-1000 mg, preferably 20 mg-500 mg, more preferably 40 mg-250 mg, particularly preferably 50 mg-200 mg.

Similarly, a single ingestion amount (effective amount) of capsaicin or capsaicinoids in the unit is generally 0.1 mg-20 mg, preferably 0.2 mg-10 mg, more preferably 0.5 mg-4 mg. For example, for ingestion twice per day, a single ingestion amount (effective amount) of capsaicin or capsaicinoids in the unit is generally 0.05 mg-10 mg, preferably 0.1 mg-5 mg, more preferably 0.25 mg-2 mg.

For example, a blood flow promoting agent comprising a unit package form for one meal, wherein the unit preferably contains 20 mg-2000 mg of citrulline or a salt thereof, and 0.1 mg-20 mg of capsaicin or capsaicinoids as a single ingestion amount (effective amount).

The blood flow promoting agent of the present invention acts on the vascular smooth muscle to expand blood vessels, and promotes blood circulation, and promotes reduction and mitigation of symptoms involving blood stagnation. Therefore, the blood flow promoting agent of the present invention can be applied to improvement of athletic performance exhibited in relation to peripheral vasodilatation, suppression of fat accumulation, improvement of skin quality, as well as securing blood circulation in ischemic disease and the like, relaxation of blood vessel biased to coarctation due to advancing age, lifestyle-related diseases and the like, prophylaxis of arteriosclerosis, and prophylaxis of stiff neck, feeling of cold, erectile dysfunction, thrombosis and the like due to blood flow disorder.

As other embodiments, a method of promoting blood flow, comprising a step of administering citrulline or a salt thereof and capsaicin or capsaicinoids to a subject in need thereof, citrulline or a salt thereof and capsaicin or capsaicinoids for use for promoting blood flow, and use of citrulline or a salt thereof and capsaicin or capsaicinoids for the production of a blood flow promoting agent are also encompassed in the present invention.

The present invention is explained in more detail in the following by referring to Examples, which are not to be construed as limitative.

EXAMPLES

Experimental Example showing investigation of the vasodilatory potency of combined use of citrulline and capsaicin is described below.

Experimental Example

The Magnus method using thoracic aorta isolated from a rat was employed for the evaluation of vasodilatory potency. 5-week-old male Wister rats (CLEA Japan, Inc.) were prelimarily bred and, after fasting for 18 hr, subjected to the experiment. L-citrulline used was manufactured by Kyowa Hakko Bio Co., Ltd. and capsaicin was purchased from Funakoshi (manufactured by BIOMOL). Under Pentobarbital anesthesia, thoracic aorta was isolated, and immersed in a Krebs-Henseleit solution (NaCl 133 mM, KCl 4.7 mM, $CaCl_2$ 2.52 mM, $KH_2PO_4$ 1.35 mM, $MgSO_4$ 0.61 mM, $NaHCO_3$ 16.3 mM, glucose 7.8 mM, pH=7.4) heated to 37±1° C. to produce an aortic ring specimen. Magnusan apparatus (Iwashiya Kishimoto Medical Instruments) was used for the measurement, Krebs-Henseleit solution warmed at 37±1° C. was filled in each well, and a 95% $O_2$-5% $CO_2$ mixed gas was aerated from below. The produced aortic ring was set on a securing needle at the well and fixed by applying tension from the inside. The well was stood for about 40 min for stabilization, and the experiment was started when the baseline of the recorder became constant. For evaluation of the vasodilatory potency, the vascular relaxation rate (%) with the addition of each sample was determined relative to Norepinephrine 0.3 μM-induced coarctation with a concentration determined by a preliminary experiment. The concentration of each sample addition, L-citrulline was set to 300 μM at which a vasodilatory action can be expected, or 1000 μM at which a higher vasodilatory action can be expected, and capsaicin was set to 1 μM at which irritant property is void as mentioned above.

FIG. 1 shows the vascular relaxation rates (%) when L-citrulline, capsaicin and a combination thereof were added.

At the addition concentration used in this test, the vasoconstriction induced by 0.3 μM Norepinephrine showed a mild relaxation action of about 7-10% by the addition of L-citrulline (300 μM) and capsaicin (1 μM). In addition, about 15-20% relaxation action was found by the addition of L-citrulline (1000 μM).

On the other hand, when L-citrulline (300 μM) and capsaicin (1 μM) were added in combination, vasodilatation was promoted as compared to single addition of each, and induction of a relaxation reaction was confirmed, showing a relaxation action of the same level as that by the addition of L-citrulline (1000 μM). Therefore, it was clarified that a combination of a low dose of capsaicin and a low dose of L-citrulline effectively enhances vasodilatation by L-citrulline, capsaicin can be used at a low dose free of irritant property, and they provide a superior blood flow promoting agent.

Preparation Examples of the present invention are shown below.

Example 1

Production of Tablet Containing Citrulline and Capsaicin

L-citrulline (120 kg), capsaicin (1.2 kg), cyclic oligosaccharide (19 kg), cellulose (57 kg) and pullulan (1 kg) are granulated in a fluid bed dryer granulator. The obtained granules and calcium stearate (3 kg) are mixed in a conical blender and compression molded by a rotary compression molding machine to give tablets.

Example 2

Production of Enteric Tablet Containing Citrulline and Capsaicin

A surface of the tablet produced in Example 1 is coated with a shellac solution to give an enteric tablet.

Example 3

Production of Enteric Capsule Containing Citrulline and Capsaicin

L-citrulline (120 kg), capsaicin (1.2 kg), cyclic oligosaccharide (19 kg), cellulose (57 kg), calcium stearate (3 kg) and pullulan (1 kg) are mixed in a conical blender. The obtained mixture (20 kg) and silicon dioxide (0.2 kg) are mixed by stirring, and the obtained mixture is fed into a capsule filling machine, and filled in hard capsules to give hard capsules. A surface of the obtained hard capsules is coated with Zein solution to give an enteric capsule.

Example 4

Production of Drinks Containing Citrulline and Capsaicin (1)

L-citrulline (1.28 kg), capsaicin (38 g), erythritol (3 kg), citric acid (0.05 kg), artificial sweetener (3 g) and flavor (0.06 kg) are dissolved by stirring in water (50 L) at a liquid temperature of 70° C., and the mixture is adjusted to pH 3.3 with citric acid, subjected to plate sterilization, filled in bottles and sterilized by a pasteurizer to give drinks.

Example 5

Production of Drinks Containing Citrulline and Capsaicin (2)

Citrulline (20 mg), capsaicin (1 mg), arginine (20 mg) and adequate amounts of fructose glucose liquid sugar, sodium chloride, citric acid, flavor, sodium citrate, calcium lactate, iron pyrophosphate, calcium gluconate, potassium chloride, magnesium chloride and sweetener are blended to give 555 ml of drinks.

Example 6

Production of Drinks Containing Citrulline and Capsaicin (3)

L-citrulline (100 mg), capsaicin (5 mg), arginine (100 mg), alanine (2.5 mg), glycine (2.5 mg), leucine (2.5 mg), isoleucine (1.3 mg), valine (1.3 mg) and adequate amounts of flavor and sweetener are blended to give 300 ml of drinks.

Example 7

Production of Skin Lotion Containing Citrulline and Capsaicin

Ethanol (10.0 wt %), L-citrulline (2.0 wt %), capsaicin (0.2 wt %), 1,3-butyleneglycol (5.0 wt %) and purified water (83.0 wt %) are blended to give skin lotion.

Example 8

Production of Cream Containing Citrulline and Capsaicin

Polyethylene glycol (PEG55), monostearate (2.00 wt %), self-emulsifying type glycerol monostearate (5.00 wt %), cetyl alcohol (4.00 wt %), squalane (6.00 wt %), triglyceryl 2-ethylhexanoate (6.00 wt %), 1,3-butyleneglycol (7.00 wt %), L-histidine (3.00 wt %), L-citrulline (1.00 wt %), capsaicin (0.05 wt %) and purified water (66.00 wt %) are blended to give cream.

Example 9

Production of Toner Containing Citrulline and Capsaicin

L-citrulline (3.00 wt %), capsaicin (0.15 wt %), water-soluble collagen (1% aqueous solution, 1.00 wt %), sodium citrate (0.10 wt %), citric acid (0.05 wt %), licorice extract (0.20 wt %), 1,3-butyleneglycol (3.00 wt %) and purified water (91.65 wt %) are blended to give toner.

Example 10

Production of Facial Mask Containing Citrulline and Capsaicin

Polyvinyl alcohol, (13.00 wt %), L-aspartic acid (1.00 wt %), L-citrulline (5.00 wt %), capsaicin (0.50 wt %), lauroylhydroxyproline (1.00 wt %), water-soluble collagen (1% aqueous solution, 2.00 wt %), 1,3-butyleneglycol (3.00 wt %), ethanol (5.00 wt %) and purified water (70.00 wt %) are blended to give facial mask.

Example 11

Production of Serum Containing Citrulline and Capsaicin

Hydroxyethylcellulose (2% aqueous solution, 12.0 wt %), xanthan gum (2% aqueous solution, 2.0 wt %), L-citrulline (2.0 wt %), capsaicin (0.1 wt %), 1,3-butyleneglycol (6.0 wt %), concentrated glycerin (4.0 wt %), sodium hyaluronate (1% aqueous solution, 5.0 wt %) and purified water (69.0 wt %) are blended to give serum.

INDUSTRIAL APPLICABILITY

The present invention provides a blood flow promoting agent comprising citrulline or a salt thereof and capsaicin or capsaicinoids as active ingredients, which enhances the effect of citrullin, and is more effective in a concentration range where capsaicin or capsaicinoids are free of irritant property, and the like.

This application is based on a patent application No. 2012-243913 filed in Japan, the contents of which are incorporated in full herein.

The invention claimed is:

1. A blood flow promoting agent comprising citrulline or a salt thereof and capsaicin or capsaicinoids as active ingredients.

2. The blood flow promoting agent according to claim 1, wherein the amount of capsaicin or capsaicinoids is 0.1 mg - 20 mg per dose for an adult.

3. The blood flow promoting agent according to claim 1, wherein the amount of citrulline or a salt thereof is 20 mg - 2000 mg per dose for an adult.

4. The blood flow promoting agent according to claim 1, wherein citrulline or a salt thereof is contained in a proportion of 10 - 200 parts by weight per 1 part by weight of capsaicin or capsaicinoids.

5. The blood flow promoting agent according to claim 4, which is in a unit package form for one meal, wherein the unit contains, as an ingestion amount for one time, 20 mg - 2000 mg of citrulline or a salt thereof, and 0.1 mg - 20 mg of capsaicin or capsaicinoids.

6. A method of promoting blood flow, comprising a step of administering citrulline or a salt thereof and capsaicin or capsaicinoids to a subject in need thereof.

7. The method according to claim 6, wherein the capsaicin or capsaicinoids is administered to the subject in an amount of 0.1 mg - 20 mg per dose for an adult.

8. The method according to claim 6, wherein the citrulline or a salt thereof is administered to the subject in an amount of 20 mg - 2000 mg per dose for an adult.

9. The method according to claim 6, wherein the citrulline or a salt thereof is administered to the subject in a proportion of 10 - 200 parts by weight per 1 part by weight of capsaicin or capsaicinoids.

10. The method according to claim 9, wherein the capsaicin or capsaicinoids is in a unit package form for one meal,
    wherein the unit contains, as an ingestion amount for one time, 20 mg - 2000 mg of citrulline or a salt thereof, and 0.1 mg - 20 mg of capsaicin or capsaicinoids.

11. The method according to claim 6, wherein the method provides for improvement of athletic performance exhibited in relation to peripheral vasodilatation, and wherein the improvement is relative to athletic performance in the absence of administering the blood flow promoting agent to the subject.

* * * * *